United States Patent
Murali

(10) Patent No.: US 8,173,979 B2
(45) Date of Patent: May 8, 2012

(54) GENERATING AND VISUALIZING AN ION BEAM PROFILE

(75) Inventor: Shettihalli Murali, Bangalore (IN)

(73) Assignee: Siemens Aktiengesellschaft, Munich (DE)

( * ) Notice: Subject to any disclaimer, the term of this patent is extended or adjusted under 35 U.S.C. 154(b) by 788 days.

(21) Appl. No.: 12/333,741

(22) Filed: Dec. 12, 2008

(65) Prior Publication Data

US 2009/0200490 A1   Aug. 13, 2009

(30) Foreign Application Priority Data

Feb. 7, 2008   (EP) .................................. 08002307

(51) Int. Cl.
 *A61N 5/00* (2006.01)
 *A61N 5/10* (2006.01)
(52) U.S. Cl. .................. 250/492.3; 250/505.1; 250/397; 250/398; 250/396 R
(58) Field of Classification Search ............... 250/492.3, 250/505.1, 397, 398, 396 R
See application file for complete search history.

(56) References Cited

U.S. PATENT DOCUMENTS

| | | | | |
|---|---|---|---|---|
| 6,690,022 B2 * | 2/2004 | Larsen et al. | ............ | 250/492.21 |
| 7,026,628 B2 * | 4/2006 | Krueger | ........................ | 250/397 |
| 7,683,347 B2 * | 3/2010 | Gupta et al. | ............ | 250/492.21 |

FOREIGN PATENT DOCUMENTS

WO    WO 91/14397    10/1991

OTHER PUBLICATIONS

EPO Communication dated Sep. 4, 2008.
Beaudre et al., "Simulation virtuelle: moyens et methodologie" ("Virtual Stimulation: Means and Methodology,") Cancer Radiotherapie: Journal de la Societe, Francaise de Radiotherapie Oncologique 1997, vol. 1, No. 5, 1997, p. 573-580, XP007905470, ISSN: 1278-3218, Elsevier, Paris, France.
Reynolds et al., "An Algorithm for Three-Dimensional Visualization of Radiation Therapy Beams," Medical Physics 1988, January-February, vol. 15, No. 1, Jan. 1998, pp. 24-28, XP007905469, ISSN:0094-2405, U.S.
Purdy et al., "Advances in 3-Dimensional Radiation Treatment Planning Systems: Room-View Display with Real Time Interactivity," International Journal of Radiation Oncology, Biology, Physics, Nov. 15, 1993, vol. 27, No. 4, pp. 933-944, XP008095553, ISSN:0360-3016, U.S.
Pelizzari et al., "Volume Visualization in Radiation Treatment Planning," Critical Reviews in Diagnostic Imaging, Dec. 2000, vol. 41, No. 6,, pp. 389-396.

* cited by examiner

*Primary Examiner* — Nikita Wells
(74) *Attorney, Agent, or Firm* — Lempia Summerfield Katz LLC

(57) ABSTRACT

A method for generating and visualizing an ion beam profile is provided. The method includes specifying an incidence direction of a particle beam, specifying a target region that is to be irradiated by said particle beam, creating an ion beam profile from points that are located on a downstream side of the target region or that are located in front of the target region and project onto the contour of the target region with respect to the incidence direction, and displaying a graphical representation of the ion beam profile.

8 Claims, 3 Drawing Sheets

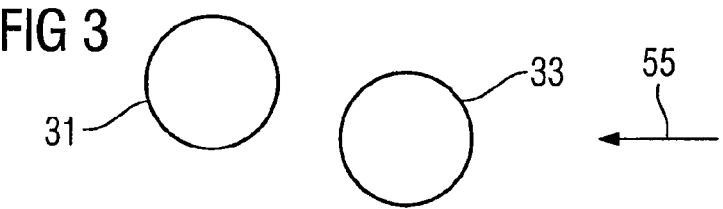
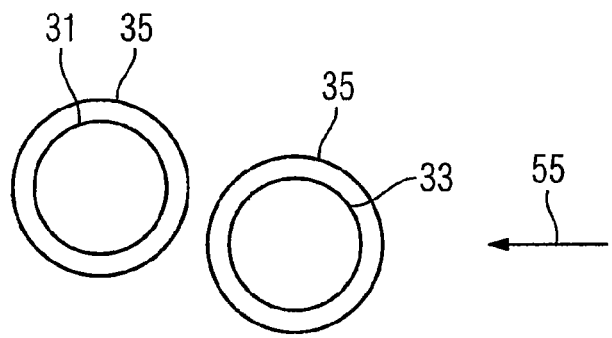
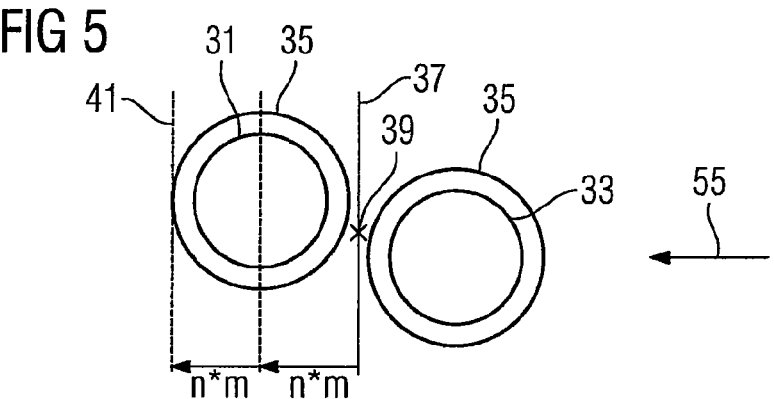
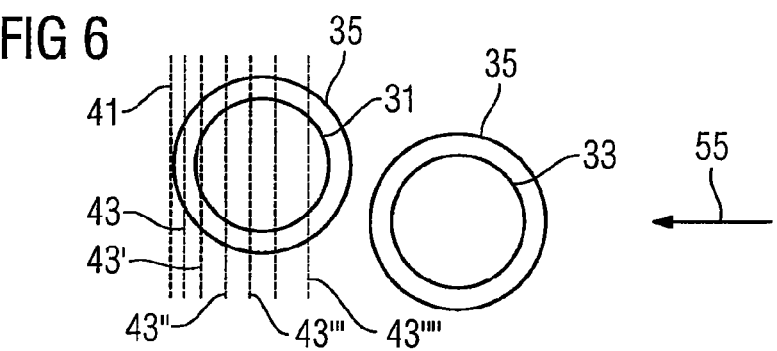

GENERATING AND VISUALIZING AN ION BEAM PROFILE

This patent document claims the benefit of European Patent Application No. EP 08002307 filed on Feb. 7, 2008, which is hereby incorporated by reference.

BACKGROUND

The present embodiments relate to generating and visualizing an ion beam profile. The ion beam profile may be used during treatment planning for a particle therapy treatment.

Particle therapy is commonly used in the field of oncology to treat localized forms of cancer and other afflictions. For particle therapy, particles such as protons, carbon ions or other particles are accelerated to high energies. The particles form a beam that is directed to a target volume. The particles of the particle beam interact with the target in a relatively delimited region resulting in localized cell damage with minimal damage of the surrounding healthy tissue. Particle therapy can be used in fields where no treatment of a patient occurs, for example, in research and development activities which involve irradiation of materials or phantoms.

Particle therapy requires accurate treatment planning. Treatment planning systems are computer-based applications used for generating treatment plans based on patient images, target definition, and machine geometry definition. Treatment planning systems allow the clinical user to visualize the three-dimensional volume of patient images, beam shapes, automatic beam shaping, placement and dose calculation.

After dose calculation, a graphical representation of the dose distribution that would affect the target volume and the surrounding tissue can be visualized. The dose distribution allows a user to verify whether the ion beam would affect the tissue in a desired way. Since dose calculation is based on the physical characteristics of an ion beam, a visualization of ion beam properties created with dose calculation algorithm also reflects the physical characteristics of an ion beam. Dose calculation, however, is time-consuming and can slow down the process of treatment planning. When a user changes parameters, such as the incidence direction of the ion beam, several times during treatment planning, the doses have to be recalculated several times.

SUMMARY AND DESCRIPTION

The present embodiments may obviate one or more of the drawbacks or limitations inherent in the related art. For example, in one embodiment, a method for generating and visualizing an ion beam profile which is fast, reliable and easy to implement and which respects the particular characteristics of an ion beam is provided. In another example, a therapy planning system and a computer software, which allows a fast and reliable determination and visualization of an ion beam profile, is provided.

In one embodiment, a method comprises: specifying an incidence direction of a particle beam, specifying a target region that is to be irradiated by the particle beam, creating an ion beam profile from points that are located on a downstream side of the target region and from points that are located in front of the target region and project onto the contour of the target region with respect to the incidence direction, and displaying a graphical representation of the ion beam profile.

The method relies on the geometrical properties of the target region and on the incidence direction of the ion beam. The method can be applied to a two-dimensional target region (e.g., leading to a two-dimensional ion beam profile) and to a three-dimensional target region (e.g., leading to a three-dimensional ion beam profile). For example, the target region can be a two or three-dimensional representation of the volume that is to be irradiated by the ion beam.

Compared to methods that visualize characteristics of an ion beam by presenting a dose distribution based on a dose calculation, the method provides a fast generation and visualization of the ion beam profile. The method does not require any dose calculation in order to create and/or to visualize an ion beam profile.

Before carrying out the method, a two or three dimensional image data set comprising an image of the target region can be provided. Such an image data set can be created, for example, by using three-dimensional medical imaging methods as computer tomography or magnetic resonance imaging. The incidence direction of a particle beam and/or the target region can then be specified using the image data set. A user may, for example, designate the incidence direction and/or the target region on images created from the image data set. For example, the target region may be generated from a set of contours delineated in images of the image data set. Accordingly, a mesh representing the target region may be created.

The created ion beam profile may reflect the typical characteristics of an ion beam. The ion beam profile, which is orthographic, has a well-defined penetration depth and it is correctly associated with the target region. The method may be used in planning software or in visualization software for oncology particle therapy systems. Accordingly, an ion beam profile may be quickly created for easy verification of the shape of the ion beam profile.

In one embodiment, the method may be used in connection with a pencil beam scanning technique. The ion beam profile may indicate how the situation would be if all the pencil beams would be switched on at the same time. The ion beam profile may indicate the complete region that gets exposed to the ion beam.

The incidence direction may, for example, be directly specified on a graphical display. For example, a user can use an input device, such as a mouse, and specify the incidence direction. The incidence direction may be specified indirectly as well, for example, by specifying the position of the beam source.

The ion beam profile may be displayed with images created from the image data set with a corresponding spatial relationship. The ion beam profile may, for example, be displayed together with structures of the object that is to be irradiated, for example, together with the target region or together with the target region and the surrounding structures. This allows a user to easily verify whether the ion beam profile passes the object at the right location.

The incidence direction of the particle beam and/or the target region can be varied several times and the ion beam profile can be re-created and re-displayed after each variation.

When the ion beam profile fits the needs of the treatment, a dose calculation can be performed based on the geometrical properties of the target region and of the incidence direction of the particle beam. Dose calculation, however, may be performed only as a last final act. After dose calculation, a graphical representation of a dose distribution can be visualized so as to precisely show how the target region at the surrounding structures would be affected by the ion beam.

The target region can comprise one single connected target volume. The method may be, however, applied to a complex target region which comprises two or more disconnected target volumes.

In one embodiment, creating the ion beam profile may include moving a virtual plane orthogonal to the incidence direction through the target region, thereby collecting contours of intersection of the virtual plane with the target region and creating the ion beam profile using the contours.

The contours of intersection of the virtual plane with the target region are used to create the ion beam profile that reflects the physical properties of the ion beam. The method may be implemented, for example, on a computer system.

In one embodiment, creating the ion beam profile may include generating a virtual plane orthogonal to the incidence direction, positioning the virtual plane through the target region at a distal edge of the target region, determining an intersection of the virtual plane with the target region, expanding the ion beam profile by the contour of the intersection, moving the virtual plane against the incidence direction of the particle beam, and repeating acts (c) to (e) until the virtual plane has completely moved through the target region.

When the virtual plane moves through the target region covering the target region, the ion beam profile expands. Accordingly, the profile constantly increases when moving from the downstream side of the target region to the upstream side of the target region.

When the ion beam profile is generated by moving the virtual plane through the target region, the contours of the intersections of the virtual planes with the target region can, for example, be used to create a mesh characterizing the ion beam profile. By repeating acts (c) to (e), the mesh gradually builds up, with an increasing contour when moving from the distal edge of the target region to the proximal edge of the target region.

The ion beam profile that is characterized by a mesh can easily be visualized on a graphical display. The mesh like structure may be represented on a graphical display.

The method may be implemented into treatment planning systems. The points contributing to the ion beam profile fulfill the requirements that they are located either on a downstream side of the target region or that they project onto the contour of the target region with respect to the incidence direction.

The treatment planning system includes at least one input device, at least one output device, and a computing unit. The treatment planning system is adapted to perform a method.

Computer software may be used to implement the method on a computer if the computer software runs on the computer. The computer software may be stored, for example, on a computer-readable medium.

BRIEF DESCRIPTION OF THE DRAWINGS

FIG. 3 to FIG. 7 illustrate acts of a method for generating and visualizing an ion beam profile.

DETAILED DESCRIPTION

Figure 1:
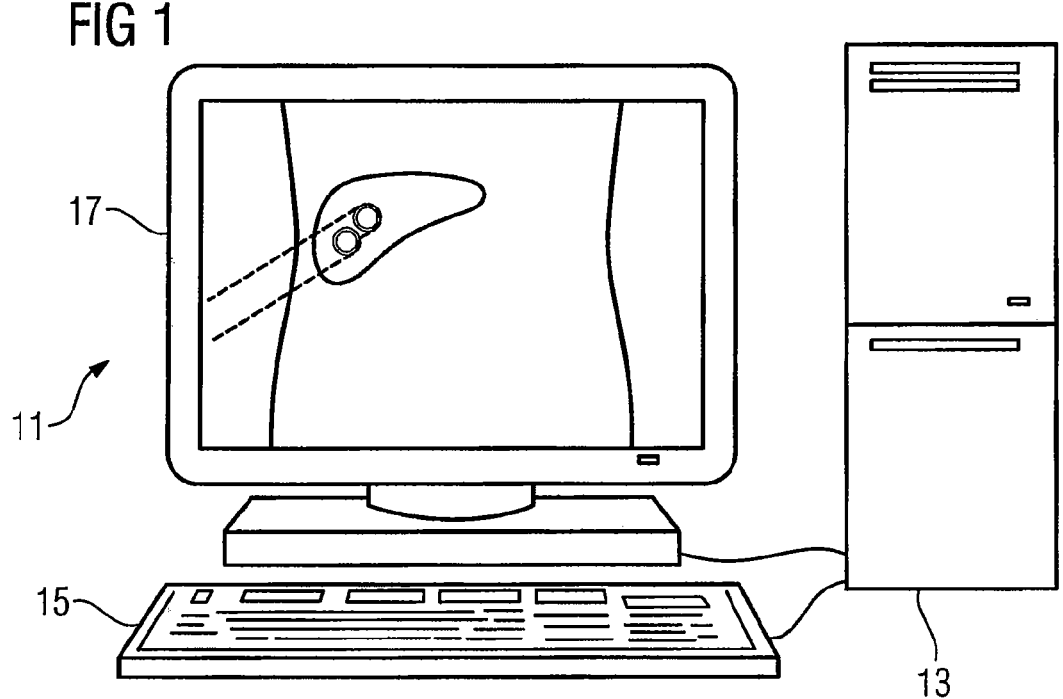
FIG. 1 shows one embodiment of a treatment planning system.

FIG. 1 shows a treatment planning system 11. The treatment planning system 11 includes a computing device 13 for performing calculations during treatment planning. The treatment planning system 11 includes at least one input device 15 that allows a user to interact with the treatment planning system 11 and at least one output device 17 for presenting information. A treatment planning system 11 may be a computer, on which appropriate treatment planning software runs.

Figure 2:
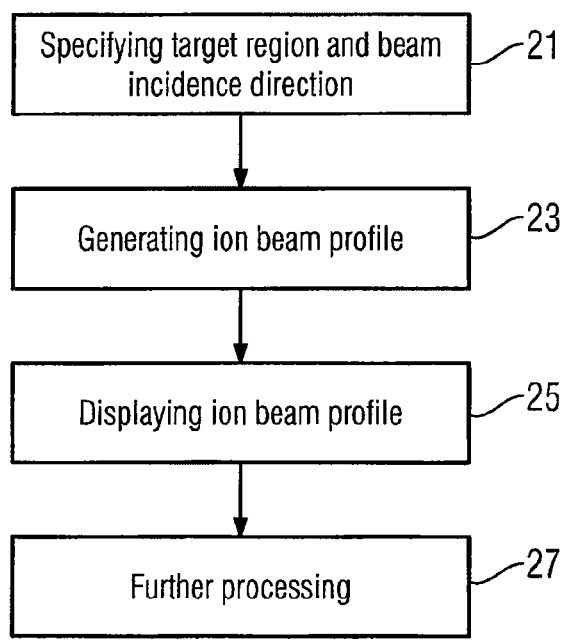
FIG. 2 shows a diagram of one embodiment of a method for generating and visualizing an ion beam profile.

FIG. 2 shows a schematic diagram of a method for generating and visualizing an ion beam profile. In act 21, a target region and an incidence direction of the particle beam are specified. The target region and/or the incidence direction of the particle beam may be specified, for example, by using images created from an image data set of an object which is to be irradiated. A user can, for example, delineate sketches of the target region on an image of the image data set by using the input device.

In act 23, the ion beam profile is generated only by using geometrical properties of the target region and its spatial relationship to the incidence direction of the particle beam. The ion beam profile is created from points that are located on a downstream side of the target region and from points that are located in front of the target region and project onto the contour of the target region with respect to the incidence direction.

After the ion beam profile has been generated, a graphical representation of the ion beam profile is displayed, as shown in act 25.

Since on the downstream side of the target region the ion beam profile is created from points which lie on the outline of the target region and since on the upstream side of the target region, the ion beam profile is created from points which project onto the contour of the target region, with respect to the incidence direction, the ion beam profile reflects the physical properties of an ion beam. Only based on geometrical properties of the target region and its spatial relationship to the incidence direction of the particle beam, the ion beam profile allows nonetheless visualizing the correct shape of the ion beam profile. If the ion beam profile is visualized together with structures of the object which is to be irradiated, a user may verify if the ion beam profile intersects with important structures.

In one embodiment, as shown in act 27, the incidence direction of the particle beam and/or the target region may be varied. Act 27 may include re-creating and re-displaying the ion beam after each variation, accepting one of the varied incidence direction and/or one of the varied target region as a final incidence direction and/or as a final target direction, respectively, and calculating a dose distribution for the ion beam based on the final incidence direction and/or on the final target region.

FIG. 3 to FIG. 6 illustrate embodiments of a method for generating and visualizing an ion beam profile in more detail.

As a first act, the target region and the beam characteristics as the source position and/or the incidence direction of the beam are specified. A predefined safety margin or a safety margin derivable from beam characteristics can be specified as well. The target region can comprise several separated target volumes. It is assumed that the target volumes are of nonzero volume. The target volumes can be listed in a target list.

In the first act, the parameters for the subsequent method acts may be specified. This can be done interactively by a user via a graphical user interface, for example.

FIG. 3 shows an example of a target region including two separated target volumes, a first target volume 31, and the second target volume 33, each of nonzero volume. The incidence direction 55 is indicated by an arrow.

As the second act, a three-dimensional margin is applied to the target region. Each of the target volumes in the target list is increased by an amount specified in the safety margin. The safety margin can, for example, be predefined or depend on specified beam characteristics. The second act gives out new targets after applying the margin on all the three directions.

This act is optional. However, if desired, it is also possible to generate an ion beam profile only based on the original target volumes.

FIG. 4 shows the target volumes of FIG. 3 which have been expanded by a (three-dimensional) margin 35. Input for the second act may include a list of targets, for example, a first target volume 31 and second target volume 33 as shown in FIG. 4. Output of the second act may include expanded target volumes after applying a (3-D) margin.

As a third act, a starting plane is identified. For collecting contours, a starting plane which should be ideally the last plane along the direction of the beam which cuts the target is to be identified. The ideal start position for identifying this plane can be the beam isocenter. At the isocenter position, a plane is created that is perpendicular to the beam direction. The ideal starting plane may be identified by cutting the target/targets from the plane to check whether it passes through any of the targets. If it cuts the target/targets, the plane is moved farther away from the beam source by n times the margin m (n is used for faster navigation purpose and is a natural number). If it does not cut the target/targets, the plane is moved towards the beam source (after confirming that there are no further targets). Repeat this until the last region in which the edge lies is identified. Identify the last plane by dividing the region into two halves and by checking in which region the edge lies.

FIG. 5 shows the expanded target volumes as shown in FIG. 4 together with a plane 37 which is orthogonal to the beam direction and passes through the beam isocenter 39. Starting from this plane 37, the ideal starting plane 41 is identified by using the algorithm described above.

Input for the third act may include an expanded target region and a plane 37 orthogonal to the beam incidence direction positioned at the beam isocenter 39 as shown in FIG. 5. Output of the third act may include a starting plane 41 as shown in FIG. 5.

As a fourth act, the contour of the ion beam profile is collected by moving the plane. The contour of the ion beam profile can be collected by cutting targets from the identified starting plane and unifying all the contours obtained. The resulting contours are collected in a separate list output contours list. The plane is moved towards the source by distance equal to the predefined margin or slightly less than margin. Since the margin may be small, no variations in target shape will be missed. Alternatively, the plane may be moved by an amount of several times of the margin. Alternatively, the plane may be moved by a distance entered by a user that is small compared to the target/targets. However, care should be taken that the amount the plane is shifted by is small enough in order to get an ion beam profile enclosing the targets completely. If the amount the plane is shifted by is too large, the ion beam profile may not cover the targets completely. The targets are cut by passing new plane collect resultant contours, projecting the contours of previous plane onto this plane, and unifying the resultant contours with the projected contours. This process is repeated until all the targets are covered. A plane is created at the beam exit point and the contours of last plane (obtained after covering all the targets) are projected and collected in the output contours list.

FIG. 6 shows gradually increasing contours as they are collected when the starting plane 41 is shifted stepwise through the target region (shifted planes 43 . . . 43'''').

Input for the fourth act may include a starting plane 41 and a predefined margin 35 as shown in FIG. 6.

Output of the fourth act may include a list of contours obtained by cutting the targets with shifted planes 43 . . . 43''''.

As a fifth act, a mesh is generated from the list of contours. All the identified contours collected in an output contours list are passed. A mesh is generated using a mesh generation algorithm. The mesh can be visualized by an ion beam 3D visualization.

Figure 7:
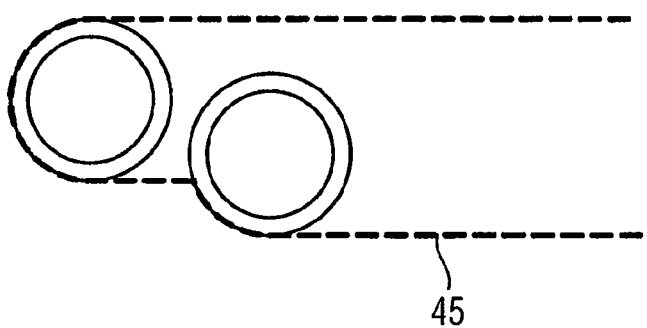

FIG. 7 shows the completed ion beam profile 45 as created by the method.

Input of the fifth act may include a list of contours.

Output from the fifth act may include a list of facets (triangles) which define a 3D ion beam profile 45 as shown in FIG. 7

Several sub-algorithms used in the method can be implemented separately. This allows a modular design of the method. Such sub-algorithms are for example:

Union Algorithm: This algorithm takes the list of contours on the same plane and gives out list of contours after applying union on input contours.

Plane Intersection Algorithm: This algorithm takes a plane and a target list and gives out list of contours as a result of intersection of plane with targets.

3D Margin Algorithm: This algorithm takes the list of targets and a predefined margin and gives out new targets after applying the margin on all the three directions.

Mesh Generation Algorithm: This algorithm takes a list of contours and generates a list of facets (triangles) by connecting the contours.

After having applied the method as described, the method outputs a list of facets which gives the three-dimensional ion beam profile.

The list of facets may be used for visualizing the three-dimensional ion beam profile by using visualization algorithms. The ion beam profile is preferably visualized together with images of the object which is to be irradiated such that a user can directly see which structures of the object are affected by the ion beam.

Figure 8:
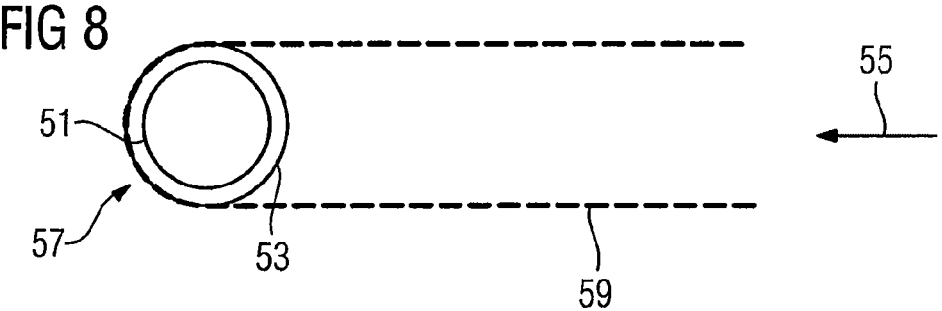
FIG. 8 to FIG. 10 show some examples of generated ion beam profiles for different constellations of target regions.
Figure 9:
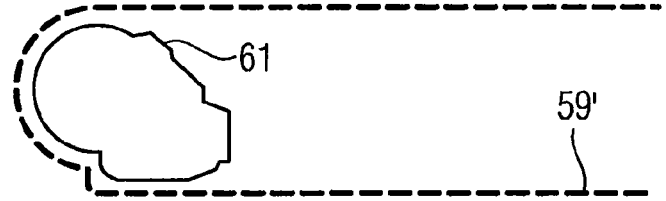
Figure 10:
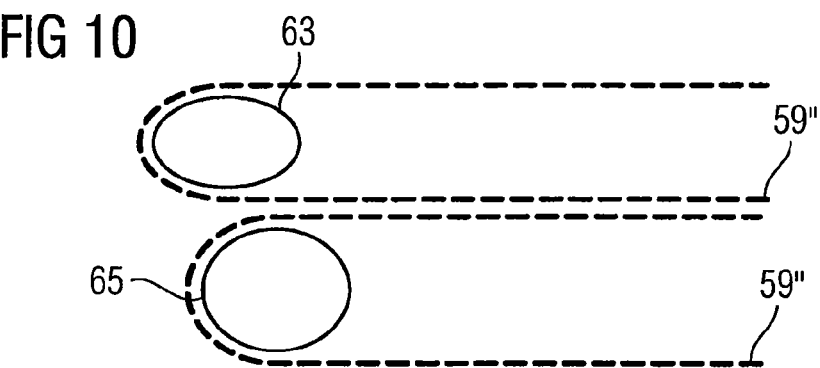

FIG. 8 to FIG. 10 shows an ion beam profile, respectively, as created by the method for different shapes of a target region other than the shape of the target region as shown in FIG. 3 to FIG. 7

FIG. 8 shows another ion beam profile 59 as generated by the method for a simple single target volume 51 that has been expanded to a target region 53 by applying a safety margin. The incidence direction 55 of the particle beam defines a downstream side 57 of the target region 53. The ion beam profile 59 includes points that are located on this downstream side of the target region 53. The ion beam profile 59 includes points that are located on the upstream side of the target region 53 if these points project with respect to the incidence direction 55 onto the contour of the target region 53.

FIG. 9 shows another ion beam profile 59' as generated by the method for a single irregular-shaped target volume 61. The target is of irregular shape such that the outer edge is broader than the inner edge. The corresponding ion beam profile 59' respects the irregular shape of the target region.

FIG. 10 shows another ion beam profile 59" for a target region which includes two separate target volumes 63, 65. In FIG. 10 the target volumes 63, 65 do not overlap when viewed from the direction of the particle beam. The ion beam profile 59" generated by the method corresponds to multiple ion beam profiles covering the clearly separated the target volumes.

Various embodiments described herein can be used alone or in combination with one another. The foregoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A method for generating and visualizing an ion beam profile, the method comprising:
   specifying an incidence direction of a particle beam;
   specifying a target region that is to be irradiated by the particle beam;
   creating the ion beam profile from points that are located on a downstream side of the target region and from points that are located in front of the target region and project onto a contour of the target region with respect to the incidence direction; and
   displaying a graphical representation of the ion beam profile.

2. The method as claimed in claim 1, wherein specifying a target region comprises:
   selecting one or more target volumes;
   expanding the one or more target volumes by a safety margin; and
   determining, as the target region, a union of the one or more expanded target volumes.

3. The method as claimed in claim 2, wherein creating the ion beam profile comprises: moving a virtual plane orthogonal to the incidence direction through the target region, thereby collecting contours of intersection of the virtual plane with the target region and creating the ion beam profile using the contours.

4. The method as claimed in claim 1, wherein creating the ion beam profile comprises: moving a virtual plane orthogonal to the incidence direction through the target region, thereby collecting contours of intersection of the virtual plane with the target region and creating the ion beam profile using the contours.

5. The method as claimed in claim 1, wherein creating the ion beam profile comprises:
   (a) generating a virtual plane orthogonal to the incidence direction;
   (b) positioning the virtual plane through the target region at a distal edge of the target region;
   (c) determining an intersection of the virtual plane with the target region;
   (d) expanding the ion beam profile by the intersection;
   (e) moving the virtual plane upstream to the incidence direction; and
   (f) repeating (c) to (e) at least until the virtual plane has moved through the target region.

6. The method as claimed in claim 5, further comprising:
   varying the incidence direction of the particle beam, the target region, or the incidence direction of the particle beam and the target region;
   re-creating and re-displaying the ion beam profile after each variation;
   accepting one of the varied incidence direction, one of the varied target region, or one of the varied incidence direction and one of the varied target region as a final incidence direction, a final target region, or the final incidence direction and the final target region; and
   calculating a dose for the ion beam based on the final incidence direction, the final target region, or the final incidence direction and the final target region.

7. A treatment planning system comprising:
   at least one input device;
   at least one output device; and
   a computing unit, the computing unit being operable to:
   specify an incidence direction of a particle beam;
   specify a target region that is to be irradiated by the particle beam;
   create an ion beam profile from points that are located on a downstream side of the target region and from points that are located in front of the target region and project onto a contour of the target region with respect to the incidence direction; and
   display a graphical representation of the ion beam profile.

8. A computer-readable medium having computer executable instructions that may be executed to:
   specify an incidence direction of a particle beam;
   specify a target region that is to be irradiated by the particle beam;
   create an ion beam profile from points that are located on a downstream side of the target region and from points that are located in front of the target region and project onto a contour of the target region with respect to the incidence direction; and
   display a graphical representation of the ion beam profile.

* * * * *